United States Patent [19]
Fernwood et al.

[11] Patent Number: 5,718,581
[45] Date of Patent: Feb. 17, 1998

[54] AIR ABRASIVE PARTICLE APPARATUS

[75] Inventors: Mark S. Fernwood; Thomas S. Blake; Craig R. Bruns, all of Danville, Calif.

[73] Assignee: Danville Manufacturing, Inc., San Ramon, Calif.

[21] Appl. No.: 438,335

[22] Filed: May 9, 1995

[51] Int. Cl.⁶ .................................................. A61C 3/02
[52] U.S. Cl. ...................... 433/88; 451/6; 451/90; 451/99; 222/196; 239/74
[58] Field of Search ................... 433/88; 451/6, 451/75, 90, 91, 99; 239/144, 311, 317, 74; 222/161, 196

[56] References Cited

U.S. PATENT DOCUMENTS

| | | | |
|---|---|---|---|
| 2,661,537 | 12/1953 | Angell | 433/88 |
| 2,696,049 | 12/1954 | Black . | |
| 2,738,234 | 3/1956 | Anderson | 302/56 |
| 2,759,266 | 8/1956 | Cassani . | |
| 2,814,877 | 12/1957 | Tilden . | |
| 3,139,705 | 7/1964 | Histed | 51/8 |
| 3,149,759 | 9/1964 | Manley | 222/193 |
| 3,344,524 | 10/1967 | Kulischenko . | |
| 3,534,503 | 10/1970 | Kulischenko | 51/8 |
| 3,631,631 | 1/1972 | Greenstein | 51/8 |
| 3,852,918 | 12/1974 | Black | 51/12 |
| 3,882,638 | 5/1975 | Black | 51/12 |
| 3,920,155 | 11/1975 | Whited | 222/161 |
| 4,067,150 | 1/1978 | Merrigan | 51/436 |
| 4,482,322 | 11/1984 | Hain et al. | 433/88 |
| 4,487,582 | 12/1984 | Warrin | 433/88 |
| 4,494,932 | 1/1985 | Rzewinski | 433/88 |
| 4,522,237 | 6/1985 | Endo et al. | 141/95 |
| 4,708,534 | 11/1987 | Gallant | 406/75 |
| 4,733,503 | 3/1988 | Gallant | 51/410 |
| 5,178,496 | 1/1993 | Trieb et al. | 406/14 |
| 5,330,354 | 7/1994 | Gallant | 433/88 |
| 5,350,299 | 9/1994 | Gallant | 433/88 |
| 5,525,058 | 6/1996 | Gallant et al. | 433/88 |

FOREIGN PATENT DOCUMENTS

PCT/US93/
02939   3/1993   WIPO .

OTHER PUBLICATIONS

Malcolm, J.A., The "Airbrasive Technique", A Manual, 1953, pp. 4–54.

S.S. White Dental Mfg. Co., The S.S. White "Airdent" Unit, Directions for its Operation, Maintenance, Care, pp. 5–8.

Buonocore, M.G., "A Simple Method Of Increasing The Adhesion Of Acrylic Filling Materials To Enamel Surfaces", Journal of Dental Research, Dec., 1955, vol. 34, No. 6, at 849–853.

*Primary Examiner*—Cary E. O'Connor

[57] ABSTRACT

A method and apparatus for an air abrasive unit such as those used in the dental field. This method and apparatus utilizes an internal vibrator motor with vibration transmitters which transmit the vibrations throughout the abrasive jar. The abrasive pickup assembly uses pressure differentials to suck up abrasive through a screen which controls the flow rate and particle size of the abrasive flowing through the system. This system can utilize a photo optical detection system to detect the abrasive level. Alternatively, a pressure/pulse detection system may be used to measure abrasive level. Dilution of the air/abrasive mixture and "air only" modes are possible with the present system. Depressurization and mere reductions of pressure can also be accommodated.

19 Claims, 10 Drawing Sheets

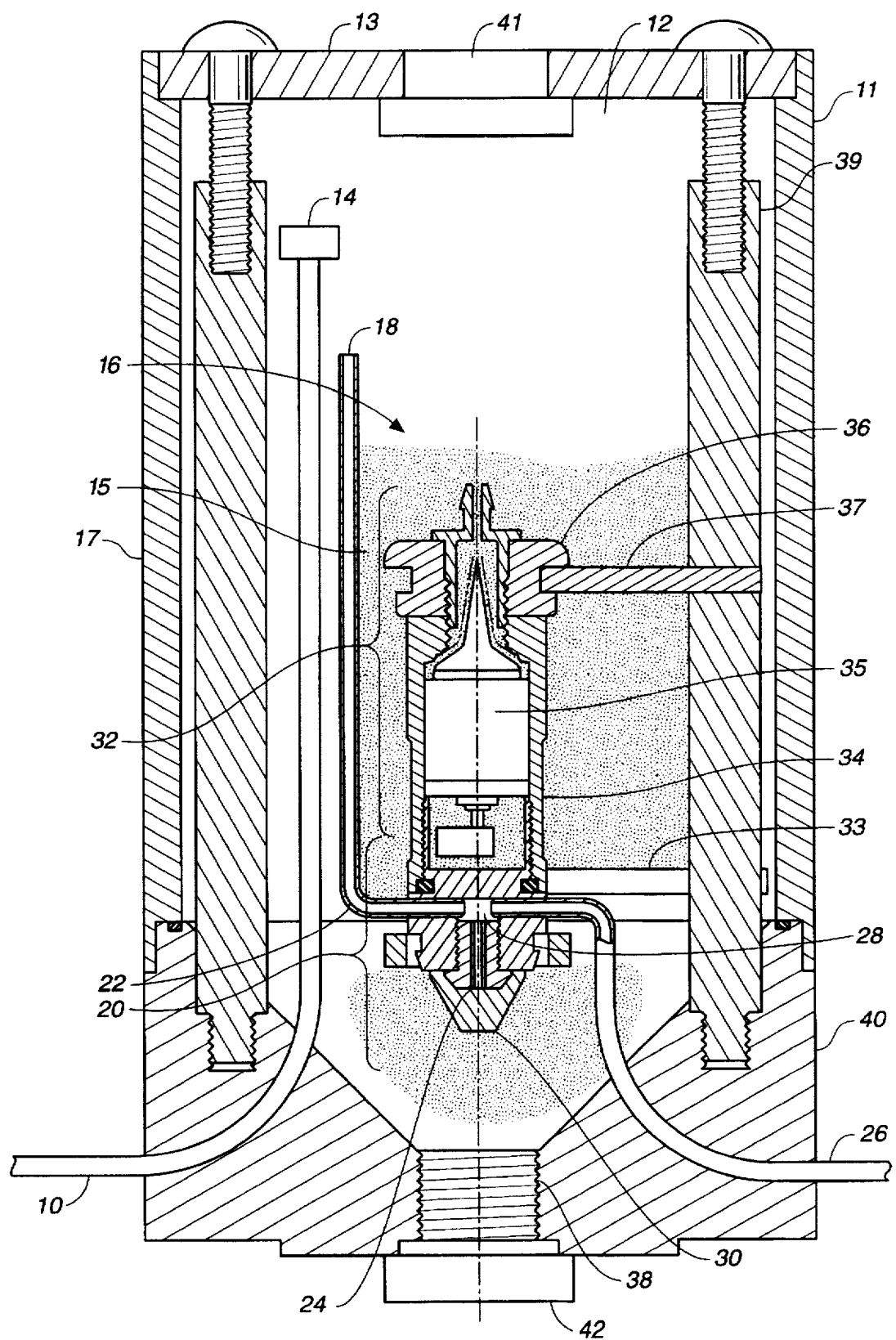
FIG._1

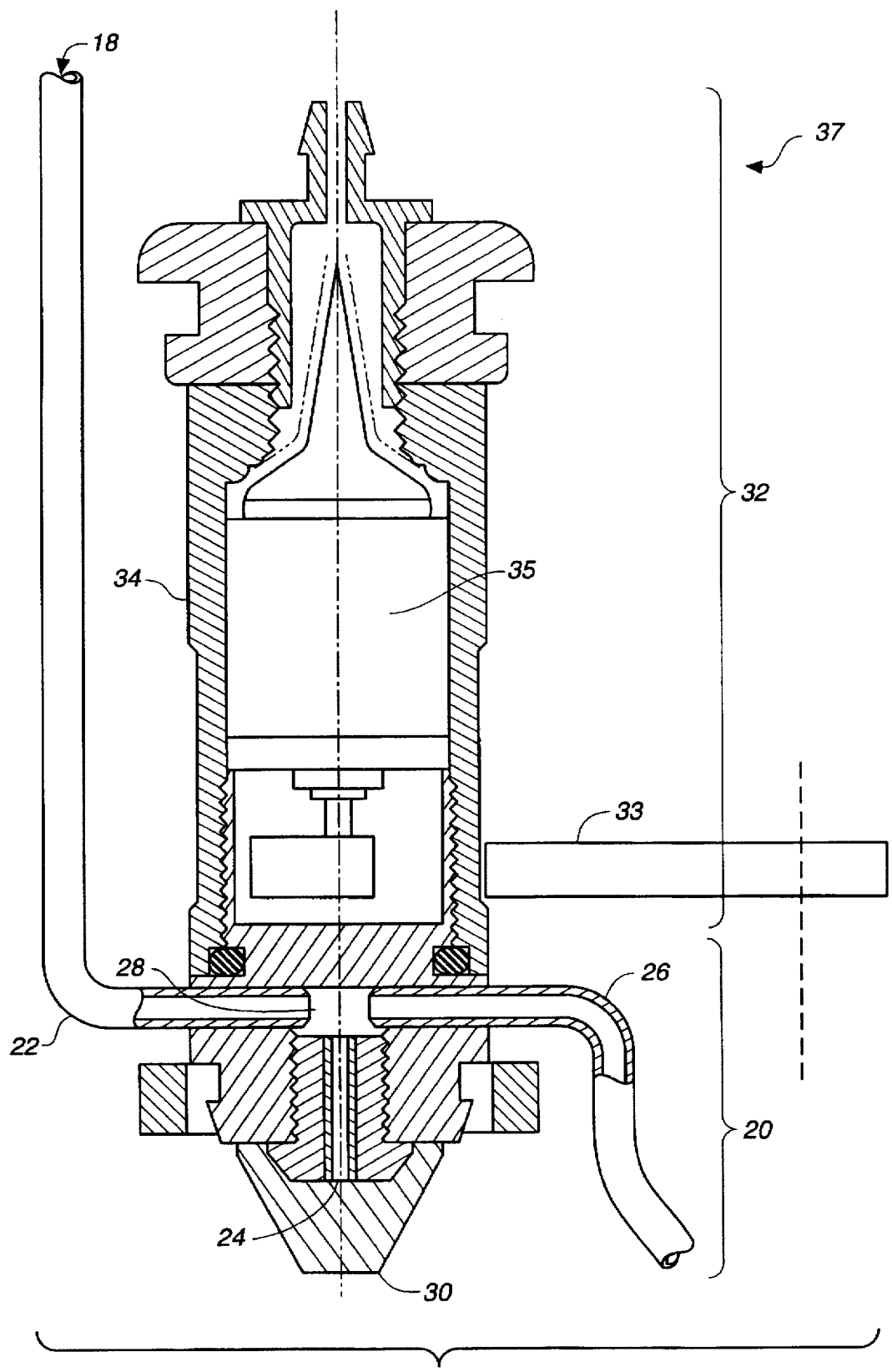
FIG._2

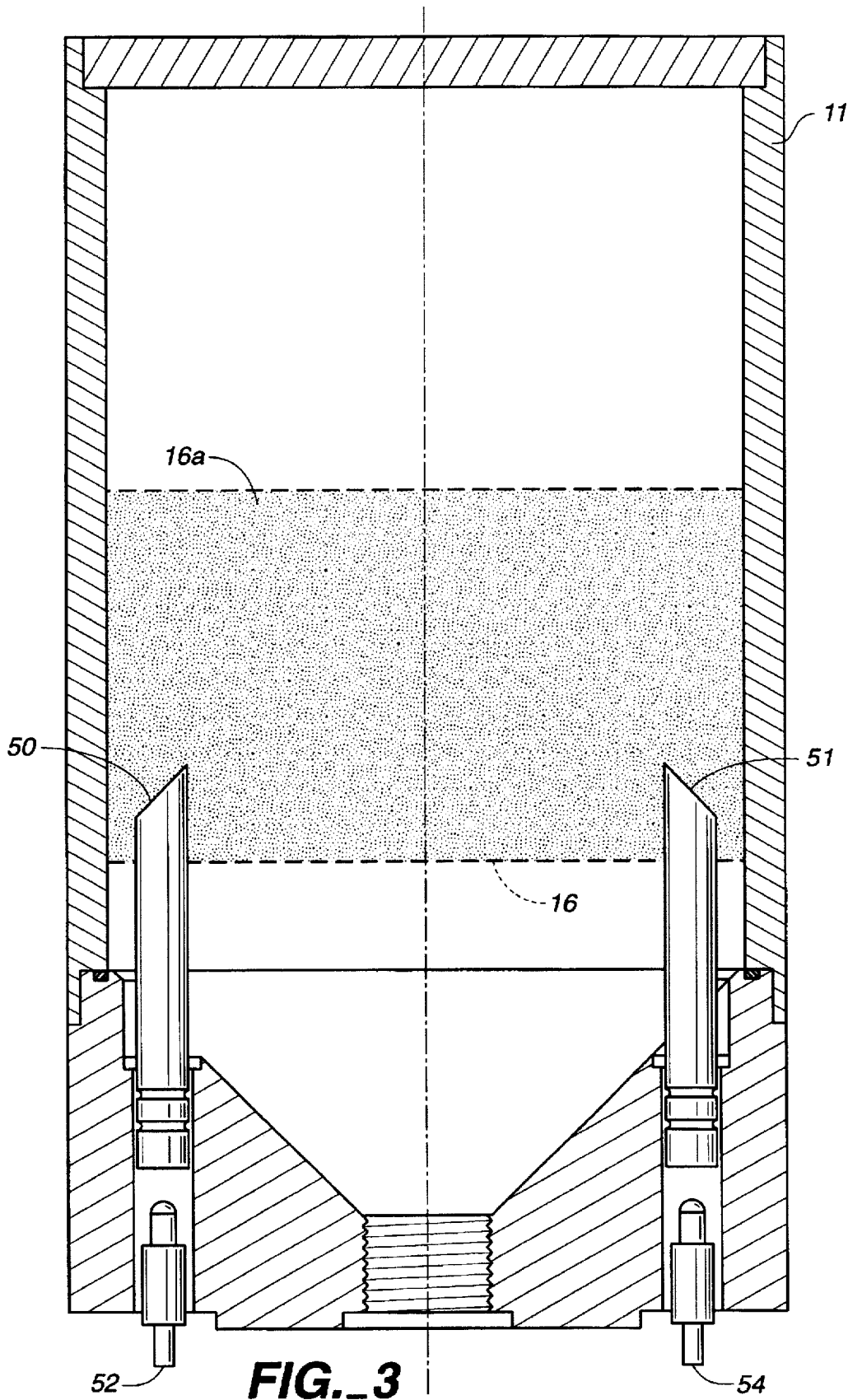
FIG._3

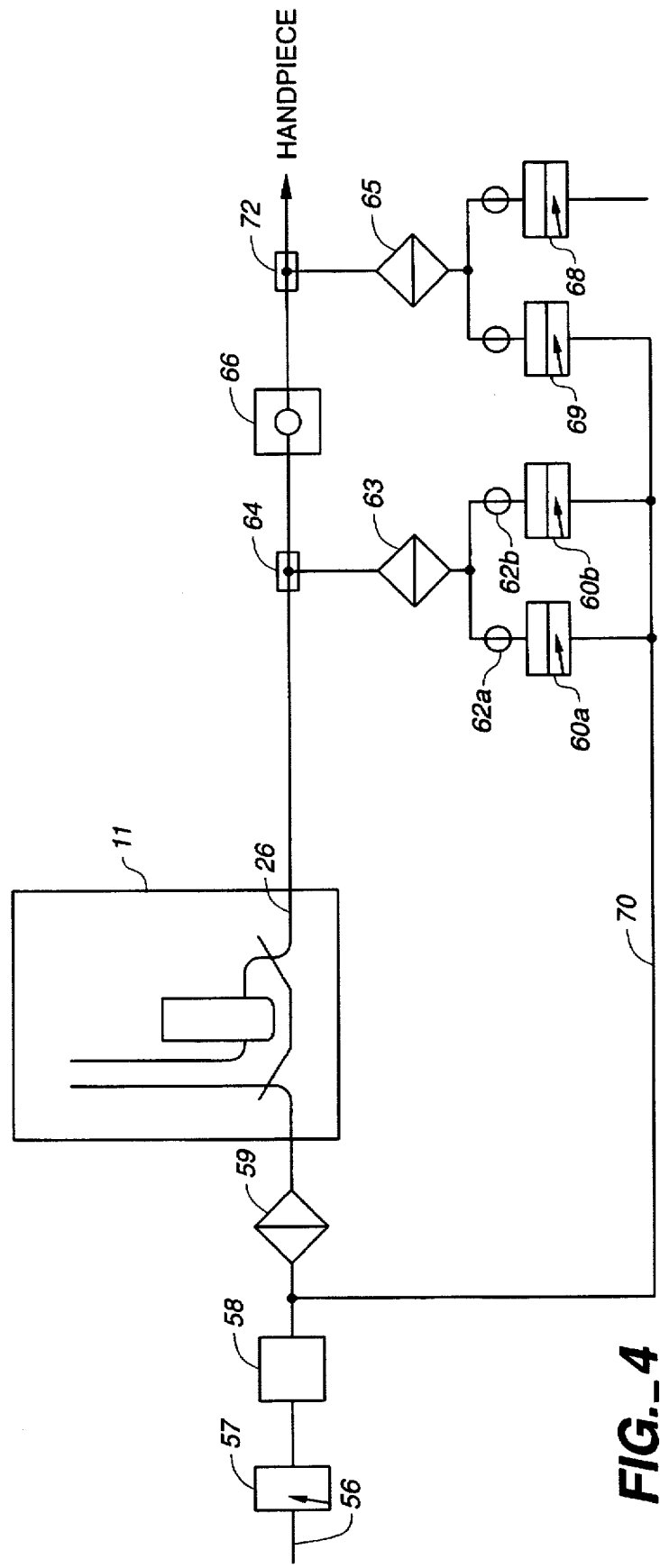
FIG._4

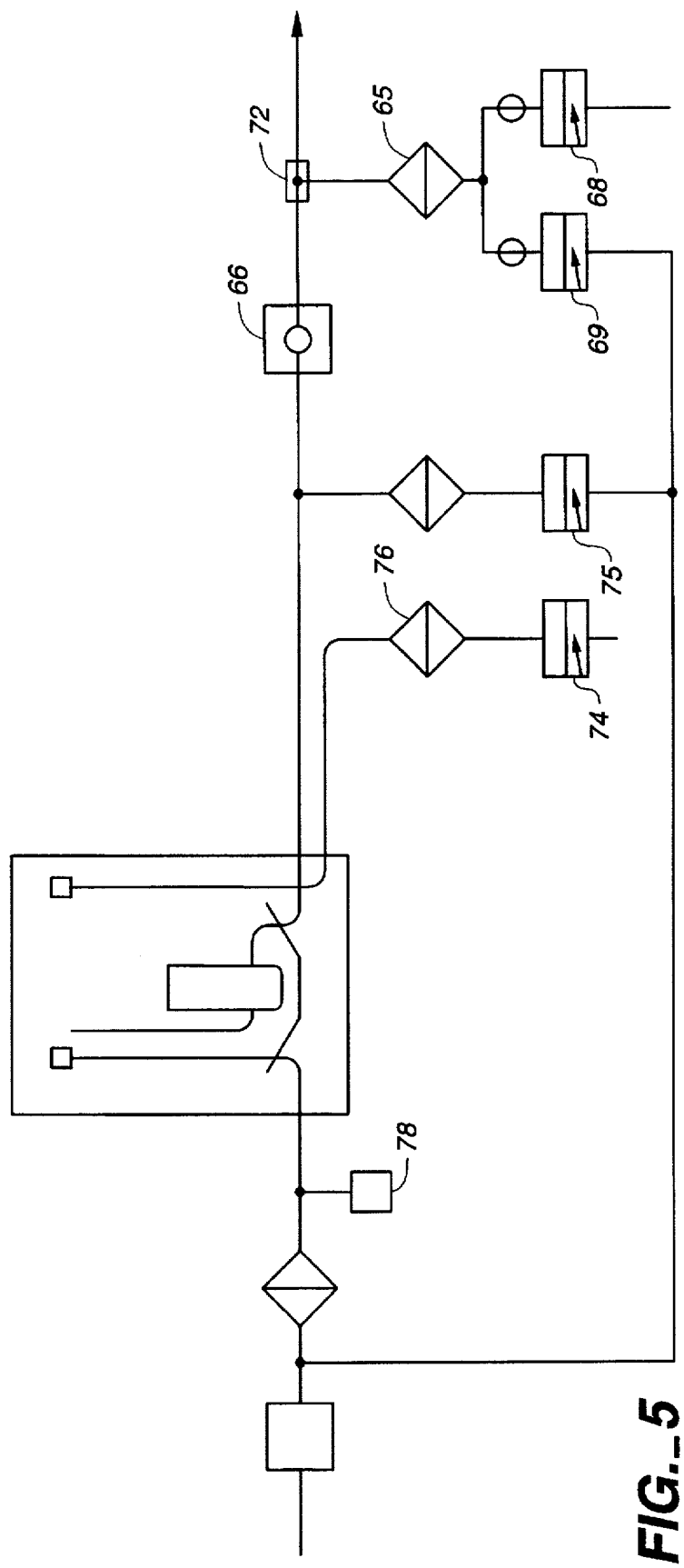
FIG._5

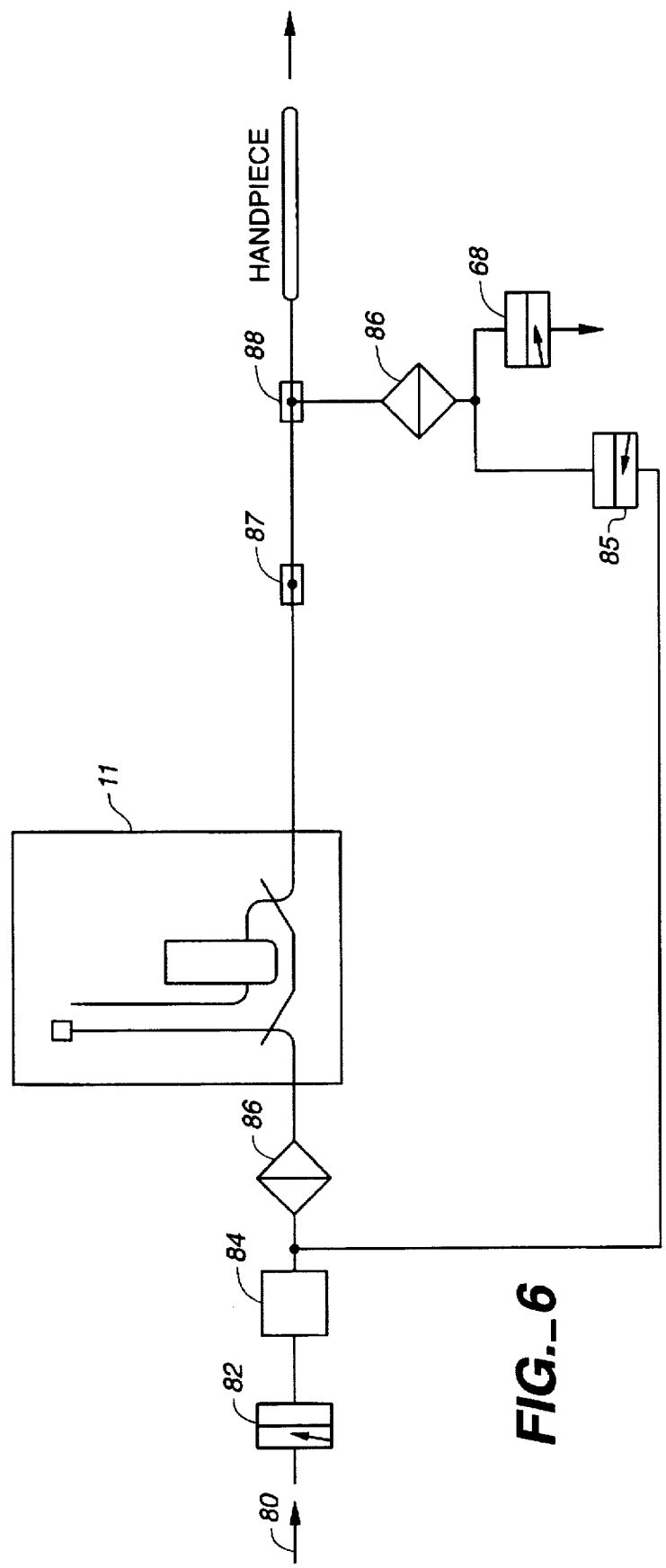
FIG._6

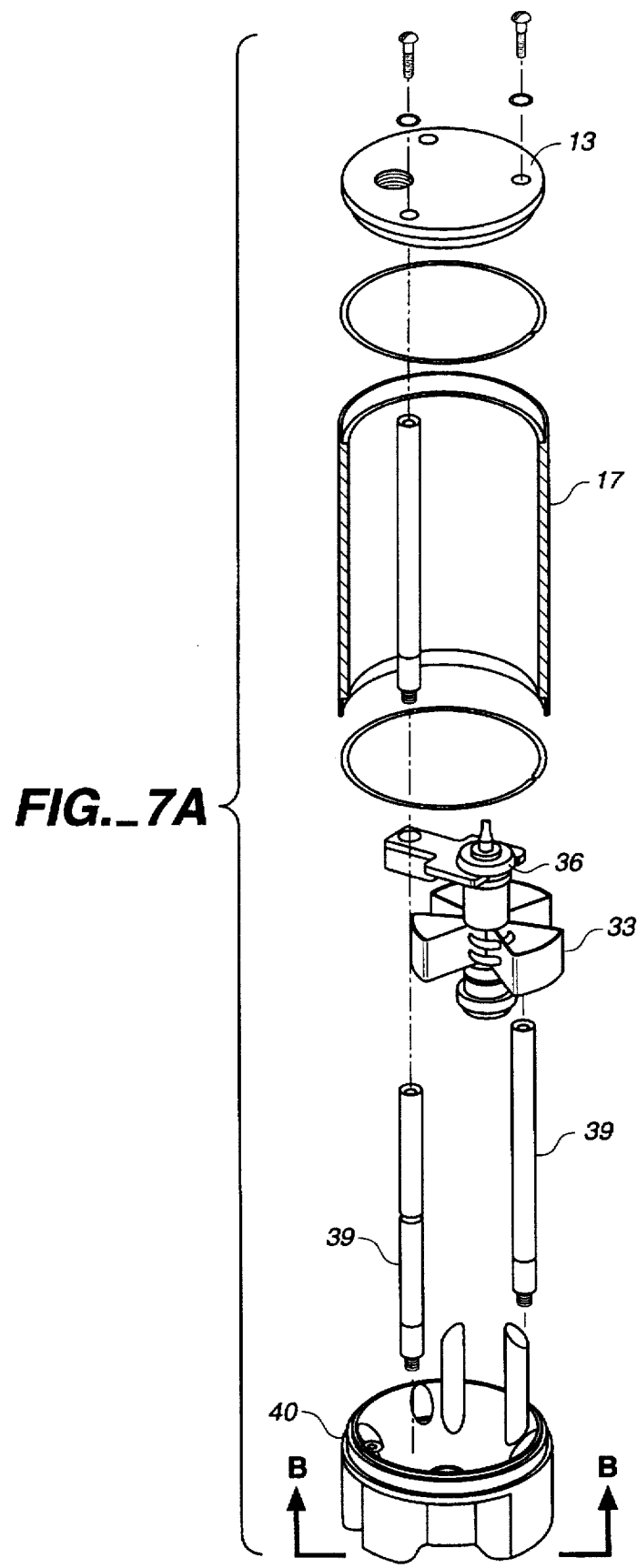
FIG._7A

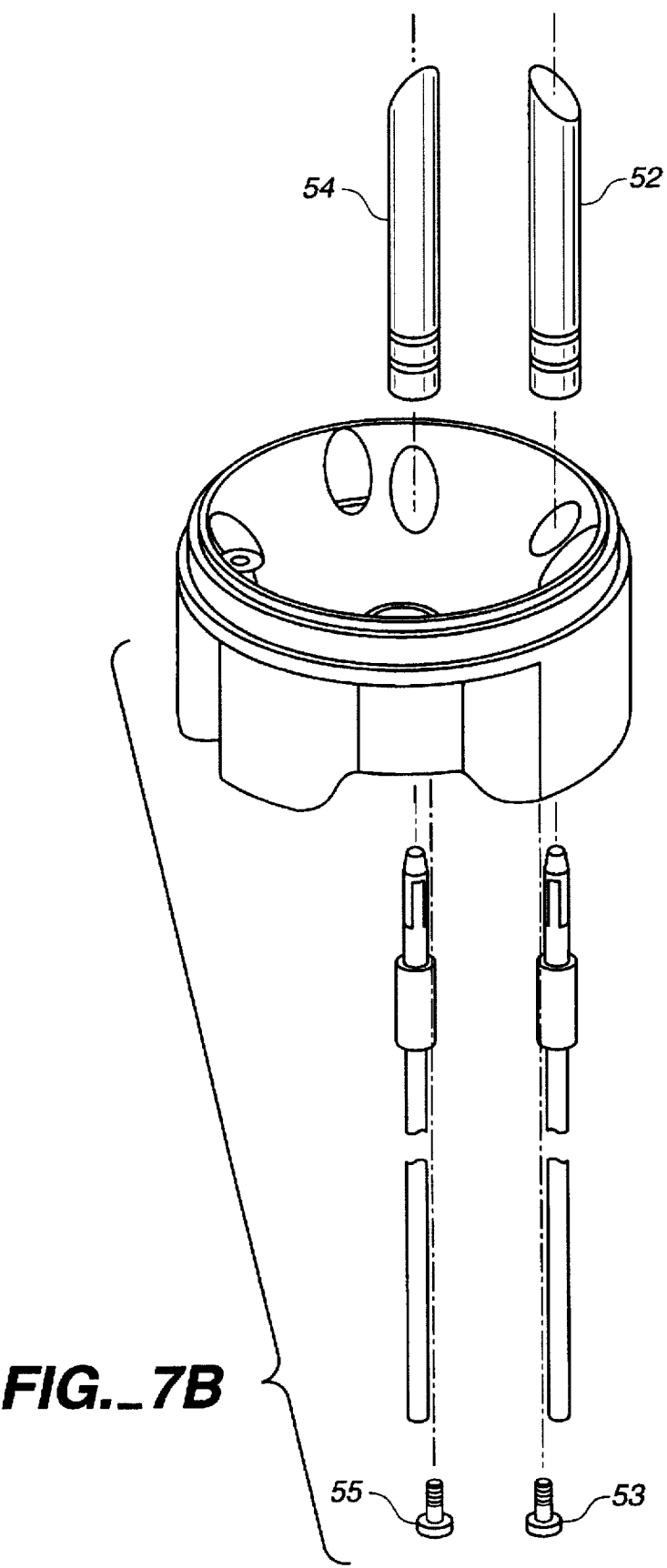
FIG._7B

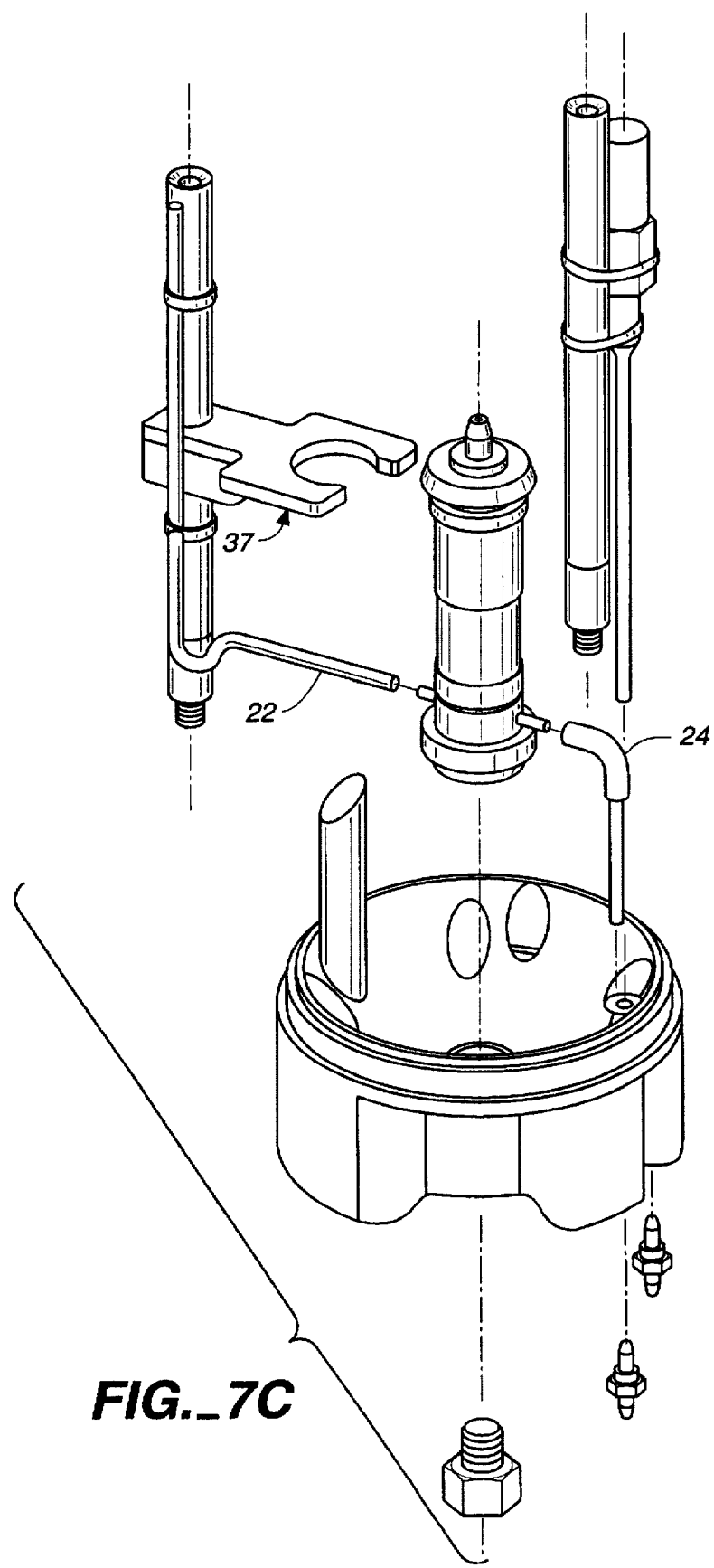
FIG._7C

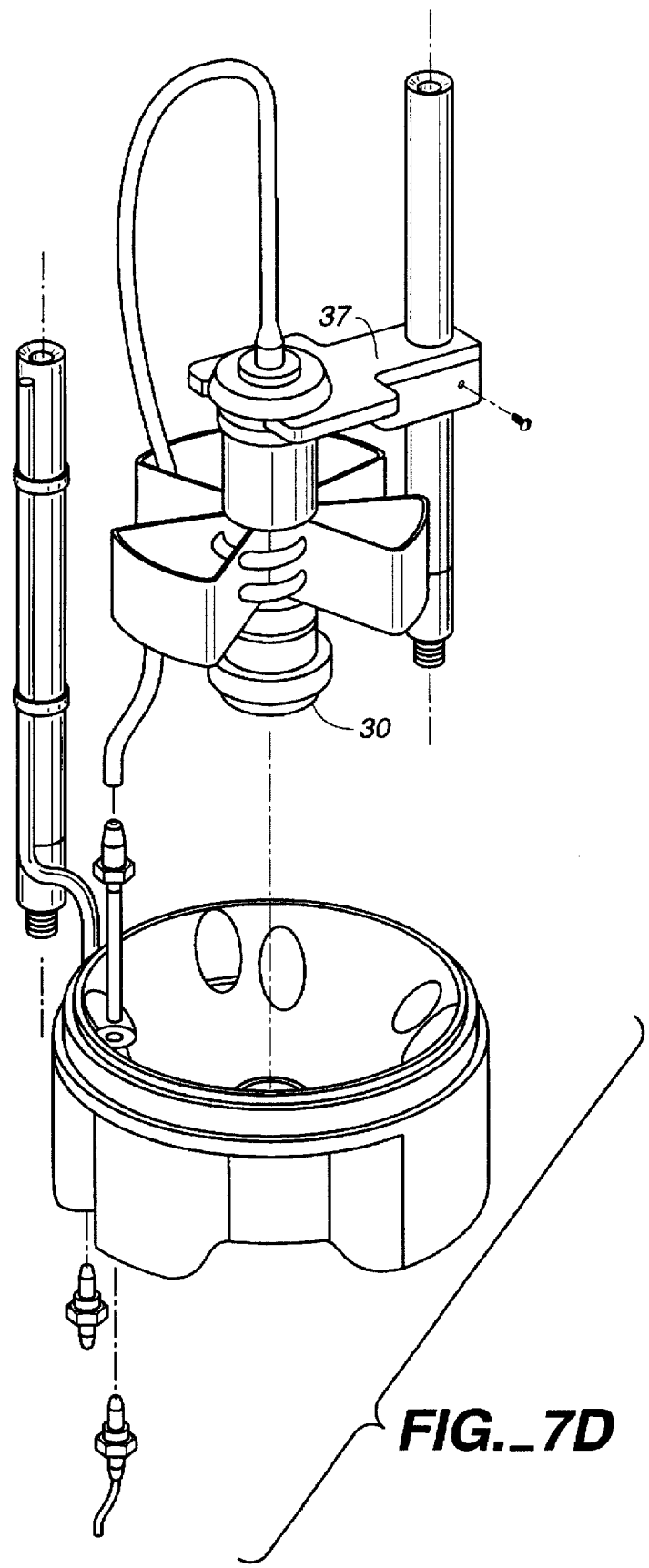
FIG._7D

5,718,581

AIR ABRASIVE PARTICLE APPARATUS

TECHNICAL FIELD

This invention relates to air abrasive technology. More particularly, it relates to methods and apparati for supplying abrasive particles to abrade a surface. The invention is particularly useful for dental applications.

BACKGROUND

The use of air abrasive in the dental industry has considerably reduced the pain and general unpleasantness involved in dental procedures. Traditional air abrasive delivery systems worked much like a salt shaker. They were basically chambers which would be vibrated in order to force the abrasive to out of the holes at the bottom of the chamber. Another type of air abrasive delivery system vibrated the abrasive to flow up through a circular track to bring sand up through the top of the chamber. These systems had the common problem of excessive noise and vibration. Systems can be found which avoid the excessive noise and vibration by blowing air over the top of the abrasive to create a dust cloud which could be blown or sucked out to the end piece. These systems had severe difficulty with abrasive flow control.

SUMMARY OF THE INVENTION

One aspect of this invention is a device for producing a pressurized stream of a gas and suspended particles, which device comprises a chamber, an inlet tube for allowing particles from a particle source to flow to the chamber, the tube having a proximal end and a distal end, a separating means positioned near the distal end of the particle inlet line to prevent particles that are larger than the distal end opening of the inlet line from getting through the separating means, a gas inlet tube for allowing a gas to enter the chamber under pressure, said gas inlet tube having a proximal end and a distal end, and an outlet tube from said chamber for allowing a stream of fluidized particles to exit the chamber, wherein when the gas is forced through the gas inlet tube to enter the chamber and it flows across the proximal end of the particle inlet tube to create a low pressure region in the chamber which allows particles to flow through the separating means and the distal end of the particle inlet tube through the proximal end of the inlet tube and into the chamber where the particles are suspended within the chamber and forced out through the outlet tube under pressure in a stream of particles suspended in the gas.

Another aspect of this invention is a vibrator assembly that comprises a motor for producing vibrations in the assembly, a housing enclosing the motor, a vibration transmitting member attached to the housing and extending radially outward of the housing, a flexible collar extending around at least a portion of the housing, a bracket to fit around the collar and securely hold the collar and housing, and at the same time attach to a member to hold the assembly in place, wherein when the motor is provided with a source of power the assembly is caused to vibrate and the vibrations are transmitted away from the assembly through the vibration transmitting member.

Another aspect of this invention is a container suitable for holding a mass of flowable particles wherein said container is defined by top, bottom, and side walls, and positioned internally in the container is a vibrator assembly housing a motor which causes the internal vibrator assembly to vibrate, the internal vibrator assembly having at least one vibration transmitting member extending from the periphery of the assembly towards the sides of the container such that the vibrations of the assembly are distributed throughout the container so that when the container is filled with flowable particles the vibrational energy is distributed to the mass of the flowable particles such that as flowable particles are removed from the lower part of the container the level of the mass of flowable particulate material recedes at a relatively uniform rate with minimum cavitation occurring within the container.

Another aspect of this invention is a container defined by top, bottom, and side walls wherein said container is suitable for holding flowable particles within the container having a means for metering material out of said container from a lower portion of the container is located within the container, a vibrator assembly is located internal to said container and is designed to distribute vibrations throughout the mass of flowable particles so that the level of the flowable particulate material recedes at a relatively constant rate and an optical level sensing device is positioned within the container such that when the level of flowable particulate material drops below a predetermined level a signal is sent externally to indicate the level of the flowable particulate material within the container.

Another aspect of this invention is a dental air abrasive system comprising (a) a container, (b) a vibrator assembly positioned internally in the container, (c) a device for producing a pressurized stream of a gas and suspended particles located within the container and associated with the vibrator assembly, (d) a dental handpiece with a nozzle for directing a pressurized stream of gas/particles against a tooth surface, and (e) a transmission tube connecting the handpiece and pressurized stream of a gas and suspended particles.

Still other aspects of this invention will be apparent to one of ordinary skill in the art by reading the following specifications and claims.

BRIEF DESCRIPTION OF THE DRAWINGS

FIG. 1 is a vertical cross-sectional view of a combination of this invention comprising a container having positioned therein a vibrator assembly integrated with a device for producing a pressurized stream of gas and suspended particles.

FIG. 2 is a vertical cross-sectional view of a vibrator assembly integrated with a device for producing a pressurized stream of gas and suspended particles.

FIG. 3 is a vertical cross-sectional view of a container with an optico-electric level detecting means.

FIG. 4 is a schematic diagram of a dental air abrasive system in accordance with this invention.

FIG. 5 is an alternative schematic design for a dental air abrasive system in accordance with this invention.

FIG. 6 is an alternative schematic design for a dental air abrasive system in accordance with this invention.

FIG. 7A, 7C and 7D are exploded views of the assemblage generally shown in FIG. 1.

FIG. 7B is an exploded view of the LED and photodiode assembly of FIG. 7A.

DETAILED DESCRIPTION AND PRESENTLY PREFERRED EMBODIMENTS

A first aspect of this invention is a device that is useful in air abrasive products in which a pressurized stream of air laden with abrasive particles is forced against a surface to remove material that is coated on the surface. Such air abrasive products are used in the dental industry to prepare teeth surfaces for various applications, in the metal finishing industry to remove coatings from a metal surface prior to further coating, in the sand blasting industry to clean stone or ceramic surfaces prior to applying a protective coating or simply to clean the surface, and other industries for similar purposes. The dimensions of the working pans of the device will depend upon the purpose for which it will be used and the industry in which it will be used. While the device will be described primarily in terms that are suitable for dental applications, it is to be understood that the device can be modified to be used in other industries. Also, while the device may be described herein primarily in combination with certain other components useful in the dental industry, it is to be understood that the device may be considered as an independent unit that can be used as a replacement part for an existing air abrasive unit that may need to be upgraded to improve or modify its performance characteristics.

In a broad description the device is for delivering a pressurized stream of gas and suspended particles, which device comprises

- a chamber;
- an inlet tube for allowing particles from a particle source to flow to the chamber, the tube having a proximal end and a distal end;
- a separating means positioned near the distal end of the particle inlet line to prevent particles that are larger than the distal end opening of the inlet line from getting through the separating means;
- a gas inlet tube for allowing a gas to enter the chamber under pressure, the gas inlet tube having a proximal end and a distal end; and
- an outlet tube from said chamber for allowing a stream of fluidized particles to exit the chamber. When a pressurized gas is forced through the gas inlet tube line to enter the chamber and flow across the proximal end of the particle inlet tube, a low pressure region is created in the chamber which allows particles to flow through the separating means and the distal end of the particle inlet tube through the proximal end of the inlet tube and into the chamber where the particles are suspended within the chamber and forced out through the outlet tube under pressure in a stream of particles suspended in the gas.

FIG. 1 provides a view of the device in combination with various other components that, in combination with the device, form aspects of this invention. Broadly, the components are a pressurizable container in which flowable particles are held and in which the device is placed and a vibrating means that assists in ensuring a controlled flow of particles to the device. Turning to the details of FIG. 1, a compressed gas, such as air, flows through the pressurized air inlet 10 of jar or container 11, which is designed to be airtight and able to withstand high pressures. The pressurized gas flows through filter 14 and into the jar interior 12 that is defined by top wall 13, side walls 17 and bottom wall 40. The gas may be any suitable inert, dry gas that is used in the air abrasive industry such as carbon dioxide, nitrogen, air, and the like. Generally it is preferred that the gas is air and is dried to such an extent that it will not cause the particles to bind together as it enters the container. The gas will be pressurized to level that is appropriate to the task at hand and may be anywhere from about 30 pounds per square inch (psi) to about 200 psi. For purposes in the dental industry the pressure will vary from about 40 psi to about 180 psi, preferably no more than 80 psi. The container interior 12 contains abrasive particles 15 and the pressurized air from the air inlet 10.

The abrasive particles are of size and hardness ranges, flowability, and other characteristics that are appropriate for the purpose for which the air abrasive stream is to be used. For example, for dental purposes the particles should be of a size between about 20 microns to about 150 microns, preferably between about 25 to about 90 microns, and of a hardness of that of aluminum oxide (also referred to as alumina, commonly used for this purpose, see for example U.S. Pat. No. 2,696,049, which is incorporated herein by reference). For removal of paint alumina or silica particles are suitable in a size range of up to 200 microns. For sandblasting stone or concrete surfaces, larger particles of up to 200 microns may be used.

The device for delivering a pressurized stream of a gas and suspended particles is shown generally as 20 in combination with a vibrator motor 32 to be discussed hereinafter. The pressurized gas of the jar interior 12 flows into the distal end 18 of gas inlet tube 22, which distal end 18 is positioned above the upper level 16 of the mass of flowable particles. Air flows from the distal end 18 of gas inlet tube 22 and into a chamber 28, where the gas and particles are mixed. Particles are allowed to enter chamber 28 through a particle inlet tube 24 that has a proximal end adjacent the particles 15. Between the distal end of the particle inlet tube 24 and the particles 15 is a separating or screening means 30 that acts to prevent or filter particles that might be larger than the distal end of the particle inlet tube from plugging the distal end or lodging in the tube. The flow of the pressurized gas from jar interior 12 across the proximal end of the particle inlet tube creates a low pressure in the pickup chamber 28 to cause the abrasive particles to flow through screen 30, into the inlet tube 24 and are suspended in pickup chamber 28 before being forced out the chamber through outlet tube 26.

The flow of abrasive particles through screen 30 not only prevents overly large particles from plugging up the system, but also acts as a flow restriction to regulate quantity of abrasive flow to the pickup tube 24. The abrasive flow into the pickup tube 24 can be regulated by selecting the inside diameter of inlet tube 26 and possibly by the length of the pickup tube 24. Once the abrasive particles 15 reach the pickup chamber 28, they mix with the pressurized air flowing from the inlet tube 22. The mixture of air/abrasive particles flows out of the outlet tube 26.

It is to be understood that cross-sectional design of tubes 22, 24 and 26 may be any appropriate variety sufficient to allow air and/or particles to flow through the tubes. Thus the cross-section could be a square, polygon, ellipse or circle. For practical considerations the tubes are preferably of circular cross-section. By varying the inside cross-sectional area of the various tubes and the length of the particle inlet tube 24 the particle flow into the chamber may be regulated. In general the inside diameter of air inlet tube 22 will be about 1 millimeter (mm) to about 2.5 mm (about 0.04 inch to about 0.1 inch), preferably about 1.25 mm.

The size of the inside diameter of the particle inlet tube 24 will be about 0.4 mm to about 0.8 mm, preferably about 2.6 mm. The length of tube 24 will generally be about 4 mm to about 15 mm, preferably about 2.6 mm. The size of the inside diameter of the outlet tube 26 will be about 1.25 mm. The interior volume of chamber 28 will generally be large enough to provide consistent mixing of the particles with the pressurized air to provide a stream of particle-laden gas that can be directed against a surface such as a tooth that can be prepared for further work. The total volume of chamber 28 will be between about 30 (mm³) and about 500 mm³, preferably about 130 mm³. By adjusting the flow of gas, the size of the tubes and chamber, and the particle size, one obtains a flow of particles from the device to be suitable for the desire task. For purposes of dental application, the flow rate of particles is between about 1 grams per minutes (gpm) to about 15 gpm, preferably about 4 to about 6 gpm.

In FIG. 1 and FIG. 2, the device 20 is shown as being attached to an assembly 32 for producing vibrations within the mass of flowable particles 15. The vibration-producing assembly 32 may be pneumatically or electrically powered but is designed to produce vibrations that are distributed throughout the mass of flowable particles so that as particles 15 are removed from the interior 12 of container 11 though screen 30 and inlet tube 26, other particles relatively uniformly flow downwardly to fill up the void left by the removal of the particles. Preferably the vibrator assembly includes a vibrator motor 35 that produces the vibrations and that may be of any suitable design, but a small permanent magnet motor such as one manufactured by Micro Motors is preferred. The motor is held within a housing 34 that has a cushioned grommet or collar 36 extending around at least a portion of the housing 34. A bracket 37 fits around collar 36 to securely hold the collar and housing and at the same time attach to a tie rod shown as 39 to hold the entire vibrator in place in the interior 12 of container 11. The vibrations created by the assembly prevents the occurrence of a cavity created by the suction around the screen 30, which in turn would prevent the abrasive particles from efficiently entering into the pickup chamber 28, thereby creating sporadic, erratic, and inefficient flow of the air/abrasive mixture.

Such vibrations created by the vibrator assembly are further transmitted through at least one vibration antenna or transmitter 33, which is attached to the vibration-producing assembly 32 at housing 34 and extends radically therefrom. An embodiment of such a vibration transmitter 33, is for it to be located as low as possible in the jar interior 12 and reach out as close to the wall of the jar interior 12 as possible. The vibration transmitter 33 may be any shape such as a straight rod, a flat sheet or in the shape of a triangular "cookie cutter." Preferably, several of these are attached to the vibrator 32 of the pickup body 34 with the outer edge of the vibration transmitter 33 as close to the sidewall 17 of the jar interior 12 as possible.

While the vibrator assembly is shown to be combined with the device for delivering a pressurized stream of gas and suspended abrasive particles, it is to be understood that vibrator assembly in combination with the vibration transmitter is useful alone to maintain the favorable flow of particles under gravity feed in other industries such as the pharmaceutical or food additive industries. For example, if flowable particles are to be gravity fed from a large container into smaller containers or into capsules or a tabletting machine and the gravity flow needs to be uniform, a suitably sized vibrator assembly (including transmitter) can be placed in the large container to, in essence, perform the same role as shown in FIG. 1, namely preventing cavitation as the particles are removed from the bottom of the container. Turning again to FIGS. 1 and 2, the vibration assembly and the device for delivering a pressurized stream of gas and suspended particles are joined together by any suitable means that will allow them to stay together during the production and transmission of the vibrations throughout the mass of particles. For example, the bottom portion of the housing 34 may have a threaded female portion that receives a complementary threaded male portion of the device for producing a pressurized stream of gas and suspended particles. The entire combination is then held in place by bracket 37, which is secured to vertical support 39. When the motor 32 is turned on, the entire combination vibrates as the bracket 37 remains relatively stationary as the cushioned collar 36 flexes with the vibrations.

In the embodiment shown in FIG. 1, the jar 11 has a bottom 40 with sloped internal sides to promote abrasive low to the pickup chamber 28 and to allow easy removal of all abrasive by the use of the abrasive outlet 38. The embodiment illustrated in FIG. 1 utilizes a plug 42 for control of abrasive removal. For facilitating the adding of more abrasive in jar 11, an abrasive inlet 41 door is provided.

Turning now to another aspect of this invention in FIG. 3, one can see a means for detecting when the upper surface level 16 of the mass of particles 15 drops below a predetermined level in container 11. The upper level 16 of the mass of particles should be monitored continuously to assure that the particle inlet tube 26 is submerged in the particles and that the distal end 18 of the air inlet tube 22 is not covered by the particles. One method of determining level 16 is through photo optical detection. Light, for example a bulb or a light emitting diode (LED), is transmitted across the interior of the jar 11 at the desired height for detection. At the same height, the light is detected by a photo diode. If the particles upper level 16a is above this desired height, the light will not be observed by the photo diode. As soon as the upper surface level of the particles drops below the photodiode, a circuit is completed to provide a signal, audible or visual, that indicates more particles need to be added to container 11. Another form of photo optical detection is shown in FIG. 3. Here, light is transmitted through transparent rods 50 and 51 with opposing angled faces so that in the manner of a prism, light is reflected at right angles. Transparent rod 50 is associated with LED 52 while rod 51 is associated with photo diode 54, each of which are mounted in removable separate cartridges for easy replacement. Multiple levels of detection are possible by multiple sets of detectors.

Turning now to FIG. 4, one can see an overall scheme of an air abrasive system that is useful for a dentist to clean the surface of a tooth in preparation for further work on the tooth surface. For example, the clinical applications of the system include: tooth surface preparation prior to fissure sealing; preventive resin preparations; any pit or fissure preparation; cervical (Class V) preparations; Class III preparations; removal of old composite resins and tunnel type preparations; desensitization of cervical dentin; cleaning and dentin sealing of crown preparations prior to cementation; endodontic access (especially through a hot tooth and through porcelain); air abrading fractured porcelain and exposed metal for porcelain repair; air abrading orthodontic bands, "Maryland Bridge" type retainers, stainless steel crowns and the interior of crowns and onlays to improve wetting during cementation; and placing small undercuts in cervical erosions to be restored without further preparation. In general, the container 11 corresponds to that shown in FIG. 2, with few of the details of FIG. 2 included in FIG. 4. For purposes of this discussion, the references to the numbers of FIG. 2 will be the same for FIG. 4.

FIG. 4 illustrates a preferred embodiment of the system that allows the user to dilute the gas particle mixture from outlet tube 26. Pressurized gas flows through the inlet air conduit 56 through a solenoid valve 57 and into a pressure regulator 58. The pressurized gas then flows through filter 59 and into jar 11 where the pressurized air is mixed with abrasive particles in accordance with the above discussion.

The gas/particles mixture then flows through the outlet tube 26 and into mixing chamber 64. The gas/particles flow from the jar 11 can be diluted with additional gas for applications of reduced cutting action. This dilution can be accomplished by injecting fluid such as air into the outlet tube 26 at mixing chamber 64. Pressurized gas from the line connecting pressure regulator 58 and filter 59 flows through the dilution conduit 70 and into a single or multiple number of solenoid valves, shown as 60a and 60b, connected to pre-set flow restrictors, such as needle valves 62a and 62b. The pressurized air then goes through filter 63 and is mixed with the air/abrasive mixture in the mixing chamber 64. The dilution may also be accomplished by using a single or multiple variable valve connected to the mixing chamber 64 in the outlet tube 26. By closing the pinch valve 66, and opening a valve connected to dilution conduit 70 downstream of pinch valve 66 will allow an "air only" mode in which only pressurized air will flow through solenoid valve 69, filter 65 and mixing chamber 72 to the hand piece. It is desirable to have the gas/particles stream stopped immediately when the pinch valve is closed. However, whenever a reserve of air pressure is in the outlet tube 24, it can cause delayed shutoff. This problem can be solved by opening the dump valve 68 to more rapidly vent residual pressure.

On a regular basis, it may be necessary to depressurize the jar 11 in order to refill with particles 15 or to remove the abrasive 15. It is also necessary to be able to reduce the pressure in the jar 11 when a lower pressure is desired by the operator. FIG. 5 illustrates an embodiment which accommodates depressurization and reduction of pressure. Solenoid valve 74 can be opened and allowed to vent air until ambient pressure or the desired reduced pressure is reached. A filter 76 prevents particles 15 from flowing into the solenoid valve 74. A pressure detector 78, shown as located at the air inlet line, such as a gauge or transducer, is used to detect the container 11 pressure. Should a particle of abrasive or a foreign matter become wedged in the interior of the pickup tube 24, it will necessary to clear it to restore the powder flow. This clearance can be accomplished by a backward flow of air into the pickup chamber 28. To pressurize the pickup chamber 28 and expel the particle, the solenoid valve 74 can be opened for a short duration, typically one to two seconds, and simultaneously open the solenoid valve 75 while closing pinch valve 66. Valves 68 and 69, filter 65 and mixing chamber 72 operate essentially the same as shown in FIG. 4.

Another embodiment is illustrated in FIG. 6. The compressed gas flows from the source 80 and flows into the solenoid valve 82. The solenoid valve 82 controls both air delivery and air pressure by pulsed-duty cycle control. The system functions normally at 3–10 cycles/second and 0–100% duty cycle. The air then flows into tank 84 which evens out the pulses of air. The filter 86 prevents backward flow of particles from the container 11, while the container 11 accurately mixes compressed air with abrasive. The pinch valve 87 controls the flow of air/abrasive stream. The solenoid valve 85 which controls the air delivery to air mixture chamber 88; is also pulsed. The solenoid valve typically functions at 3–10 cycles per second and 0–100% duty cycle. The injected air from solenoid valve 85 mixes with the gas/particles stream in the mixing chamber 88 where the injected air dilutes the gas/particles mixture as the desired mixture. The diluted stream of air/abrasive then flows to the hand-piece. A dump valve 68 is optionally situated downstream of pinch valve 87 and operates as described in the FIG. 4 discussion to vent residual pressure from the line to the hand piece.

A further derailed view of the container vibrator assembly and device for producing a stream of pressurized gas air particles is shown in FIGS. 7A, 7B, 7C and 7D. Here you can more clearly see as an exploded view the various components of the system. For example, in FIG. 7A one can see how the vibrator assembly and the vibration transmitters or antennae 33 are designed in the "cookie cutter" design. This is a triangular design shown extending from the periphery of the vibrator assembly housing. One can see also the detail of the container having top 13, side wall 17 and bottom wall 40. FIG. 7B shows the LED 52 and the screw 53 which is used to attach it and its components to the bottom wall 40 of the container 11. Similarly, the photodiode of 54 is attached using screw 55. Other aspects of the details of the invention can be seen in FIGS. 7C and 7D, where it is seen where bracket 37 fits into collar or grommet 36 to hold the internal vibrator assembly in place. Further, one can see air inlet tube 22 and the outlet tube 24 along with screen 30 for the abrasive pickup assembly 20.

The invention now being fully described, it will be apparent to one of ordinary skill in the art that many changes and modifications can be made thereto without departing from the spirit or scope of the appended claims.

What is claimed is:

1. A device for producing a pressurized stream of a gas and suspended particles, which device comprises a chamber, an inlet tube for allowing particles from a particle source to flow substantially upwardly to the chamber, the tube having a proximal end and a distal end, a separating means positioned near the distal end of the particle inlet tube to prevent particles that are larger than the distal end opening of the inlet tube from getting through the separating means, a gas inlet tube for allowing a gas to enter the chamber under pressure, said gas inlet tube having a proximal end and a distal end, and an outlet tube from said chamber for allowing a stream of fluidized particles to exit the chamber, wherein when the gas is forced through the gas inlet tube to enter the chamber it flows across the proximal end of the particle inlet tube to create a low pressure region in the chamber which allows particles to flow substantially upwardly through the separating means and the distal end of the particle inlet tube through the proximal end of the inlet tube and into the chamber where the particles are suspended within the chamber and forced out through the outlet tube under pressure in a stream of particles suspended in the gas.

2. The device of claim 1 positionable in a container having upper and lower regions and suitable for holding a source of flowable particles within it under a pressure greater than 1 atmosphere, wherein the device is positionable in the container towards the lower region of the container such that when the container has such particles therein the device will be located below the upper surface of the mass of such particles, the gas inlet tube has its proximal end positioned adjacent the chamber and its distal end positioned such that it would be in the upper region of the container so that the distal end would be above the surface of the mass of flowable particles.

3. The device of claim 2 in combination with a container suitable for holding a mass of flowable particles, wherein the container has an orifice to allow pressurized gas to enter the container such that the pressurized gas flows into the container to pressurize the container with a given pressure on the surface of the mass flowable particles, the gas also entering the distal end of the gas inlet tube leading to the chamber such that the gas pressure inside of the container and the gas pressure at the entry of the proximal end of the gas inlet tube is the same as the gas pressure entering the container.

4. The combination of claim 3 wherein a vibrator assembly is associated with the container such that when the container is filled with flowable particles the vibrator assembly sends out vibrations through the mass of particles to minimize the occurrence of cavitation within the mass of particles as the particles are taken into the chamber through the particle inlet tube and forced out through the outlet tube.

5. The combination of claim 4 wherein the vibrator assembly is positioned internally to the container and comprises a motor for producing vibrations in the assembly, a housing enclosing the motor, a vibration transmitting member attached to the housing and extending radially outward of the housing, a flexible collar extending around at least a portion of the housing, a bracket to fit around the collar and securely hold the collar and housing, and at the same time attach to a member to hold the assembly in place, wherein when the motor is provided with a source of power the assembly is caused to vibrate and the vibrations are transmitted away from the assembly through the vibration transmitting member.

6. The combination of claim 3 wherein at least one means for detecting when the upper surface of the mass of particles drops below a predetermined level is incorporated to provide a signal to indicate when additional particles should be added to the container.

7. The device of claim 1 in combination with a dental handpiece having a nozzle for directing the gas/particles stream against a tooth surface, wherein the handpiece is connected to the outlet tube by a transmission tube through which the gas/particles mixture flows, the transmission tube having a control valve therein to regulate the flow of the gas/particles stream therethrough and a junction downstream of the valve for mixing additional gas with the gas/particles stream in the transmission tube and reducing the concentration of the gas/particles stream exiting the handpiece nozzle.

8. The device of claim 7 wherein the transmission tube has a second junction upstream of the control valve for mixing additional gas with the gas/particles stream to further reduce the concentration of the gas/particles stream prior to reaching the control valve.

9. A vibrator assembly that comprises a motor for producing vibrations in the assembly, a housing enclosing the motor, a vibration transmitting member attached to the housing and extending radially outward of the housing, a flexible collar extending around at least a portion of the housing, a bracket to fit around the collar and securely hold the collar and housing, and at the same time attach to a member to hold the assembly in place, wherein when the motor is provided with a source of power the assembly is caused to vibrate and the vibrations are transmitted away from the assembly through the vibration transmitting member.

10. A container suitable for holding a mass of flowable particles wherein said container is defined by top, bottom, and side walls, and positioned internally in the container is a vibrator assembly housing a motor which causes the internal vibrator assembly to vibrate, the internal vibrator assembly having at least one vibration transmitting member extending from the periphery of the assembly towards the sides of the container such that the vibrations of the assembly are distributed throughout the container so that when the container is filled with flowable particles the vibrational energy is distributed to the mass of the flowable particles such that as flowable particles are removed from the lower part of the container the level of the mass of flowable particulate material recedes at a relatively uniform rate with minimum cavitation occurring within the container.

11. The device of claim 10 wherein the vibratory motor is electrically driven.

12. The device of claim 11 wherein the vibratory motor is pneumatically driven.

13. The device of claim 10 wherein the vibration transmitter is fixedly attached to the vibratory assembly and radially emanate from the assembly.

14. The container and vibrator assembly of claim 10 wherein the vibrator assembly comprises a motor for producing vibrations in the assembly, a housing enclosing the motor, a vibration transmitting member attached to the housing and extending radially outward of the housing, a flexible collar extending around at least a portion of the housing, a bracket to fit around the collar and securely hold the collar and housing, and at the same time attach to a member to hold the assembly in place.

15. The container and vibrator assembly of claim 14 wherein a device for producing a pressured stream of a gas and suspended particles is integrated with the vibrator assembly, wherein said device comprises a chamber, an inlet tube for allowing particles from a particle source to flow to the chamber, the tube having a proximal end and a distal end, a separating means positioned near the distal end of the particle inlet tube to prevent particles that are larger than the distal end opening of the inlet line from getting through the separating means, a gas inlet tube for allowing a gas to enter the chamber under pressure, said gas inlet tube having a proximal end and a distal end, and an outlet tube from said chamber for allowing a stream of fluidized particles to exit the chamber, wherein when the gas is forced through the gas inlet tube to enter the chamber it flows across the proximal end of the particle inlet tube to create a low pressure region in the chamber which allows particles to flow through the separating means and the distal end of the particle inlet tube through the proximal end of the inlet tube and into the chamber where the particles are suspended within the chamber and forced out through the outlet tube under pressure in a stream of particles suspended in the gas.

16. A dental air abrasive system that comprises (a) a container defined by top, bottom and side walls suitable for holding flowable particles therein, (b) positioned internally in the container is a vibrator assembly housing a motor which causes the internal vibrator assembly to vibrate such that the vibrations of the assembly are distributed throughout the container so that when the container is filled with flowable particles the vibrational energy is distributed to the mass of the flowable particles such that as flowable particles are removed from the lower part of the container the level of the mass of flowable particulate material recedes at a relatively uniform rate with minimum cavitation occurring within the container, (c) a device for producing a pressurized stream of a gas and suspended particles, which device comprises a chamber, an inlet tube for allowing particles from a particle source to flow to the chamber, the tube having a proximal end and a distal end, a separating means positioned near the distal end of the particle inlet tube to prevent particles that are larger than the distal end opening of the inlet line from getting through the separating means, a gas inlet tube for allowing a gas to enter the chamber under pressure, said gas inlet tube having a proximal end and a distal end, and an outlet tube from said chamber for allowing a stream of fluidized particles to exit the chamber, wherein when the gas is forced through the gas inlet tube to enter the chamber it flows across the proximal end of the particle inlet tube to create a low pressure region in the chamber which allows particles to flow through the separating means and the distal end of the particle inlet tube through the proximal end of the inlet tube and into the chamber where the particles are suspended within the chamber and forced out through the outlet tube under pressure in a stream of particles suspended in the gas, (d) a handpiece with a nozzle for directing a pressurized stream of gas/particles against a tooth surface, and (e) a transmission tube connecting the handpiece and, the outlet tube, wherein the transmission tube has a control valve between the outlet tube and the handpiece to regulate the flow of gas/particles stream therethrough.

17. The dental air abrasive system of claim 16 wherein the internal vibrator assembly has at least one vibration transmitting member extending from the periphery of the assembly towards the sides of the container.

18. A device for producing a pressurized stream of a gas and suspended particles, which device comprises a chamber, an inlet tube for allowing particles from a particle source to flow substantially upwardly to the chamber, the tube having a proximal end and a distal end, a gas inlet tube for allowing a gas to enter the chamber under pressure, said gas inlet tube having a proximal end and a distal end, and an outlet tube from said chamber for allowing a stream of fluidized particles to exit the chamber, wherein when the gas is forced through the gas inlet tube to enter the chamber it flows across the proximal end of the particle inlet tube to create a low pressure region in the chamber which allows particles to flow through the distal end of the particle inlet tube through the proximal end of the inlet tube and into the chamber where the particles are suspended within the chamber and forced out through the outlet tube under pressure in a stream of particles suspended in the gas.

19. An air abrasive system that comprises a container for holding particles, a vibrator positioned within the container, a device coupled to the container for producing a pressurized stream of particles, a handpiece to deliver the pressurized stream of particles, a transmission conduit connecting the pressurized stream of particles and the handpiece, a valve positioned in the transmission conduit, and a dump valve downstream of the valve in the transmission conduit to vent the residual pressure in the transmission conduit.

\* \* \* \* \*